(12) United States Patent
Babcock et al.

(10) Patent No.: US 11,000,624 B1
(45) Date of Patent: May 11, 2021

(54) FACE COVERING WITH ULTRAVIOLET EMITTER

(71) Applicant: UVC Protection LLC, Eden, UT (US)

(72) Inventors: Ryan L. Babcock, Ogden, UT (US); John W. Babcock, Eden, UT (US)

(73) Assignee: UVC PROTECTION LLC, Eden, UT (US)

( * ) Notice: Subject to any disclaimer, the term of this patent is extended or adjusted under 35 U.S.C. 154(b) by 0 days.

(21) Appl. No.: 16/931,836

(22) Filed: Jul. 17, 2020

Related U.S. Application Data

(60) Provisional application No. 63/006,839, filed on Apr. 8, 2020, provisional application No. 62/983,089, filed on Feb. 28, 2020.

(51) Int. Cl.
*A61L 9/20* (2006.01)
*A41D 13/11* (2006.01)

(52) U.S. Cl.
CPC ............ *A61L 9/20* (2013.01); *A41D 13/1161* (2013.01); *A61L 2209/12* (2013.01); *A61L 2209/15* (2013.01)

(58) Field of Classification Search
CPC .... A61L 9/20; A61L 2209/12; A61L 2209/15; A41D 13/1161
See application file for complete search history.

(56) References Cited

U.S. PATENT DOCUMENTS

| 4,806,768 | A | 2/1989 | Keutenedjian |
| 5,165,395 | A | 11/1992 | Ricci |
| 5,855,203 | A | 1/1999 | Matter |
| 6,233,748 | B1 | 5/2001 | Gieger et al. |
| 6,470,888 | B1 | 10/2002 | Matter |
| 6,681,765 | B2 | 1/2004 | Wen |
| 8,733,356 | B1 * | 5/2014 | Roth .......................... A61L 9/20 128/205.27 |
| 2007/0163588 | A1 | 7/2007 | Hebrank et al. |
| 2009/0004047 | A1 | 1/2009 | Hunter et al. |
| 2009/0205664 | A1 | 8/2009 | Lyon |
| 2012/0279503 | A1 | 11/2012 | Zhou et al. |
| 2015/0128935 | A1 | 5/2015 | Lemper |
| 2018/0214585 | A1 * | 8/2018 | Piper ....................... C02F 1/325 |
| 2018/0339073 | A1 * | 11/2018 | Clynne ..................... A61L 2/10 |
| 2019/0062177 | A1 * | 2/2019 | Blad ......................... C02F 1/28 |
| 2019/0117820 | A1 * | 4/2019 | Dam ....................... F24F 11/30 |
| 2019/0365941 | A1 * | 12/2019 | Elrod ....................... A61L 9/20 |
| 2020/0171184 | A1 * | 6/2020 | Tanaka ..................... A61L 2/10 |

OTHER PUBLICATIONS fda.gov, "N95 Respirators, Surgical Masks, and Face Masks" (Year: 2021).*
TaoYuan UVC LED (Year: 2019).*

* cited by examiner

*Primary Examiner* — Sean E Conley
*Assistant Examiner* — Brendan A Hensel
(74) *Attorney, Agent, or Firm* — Kunzler Bean & Adamson; Bruce R. Needham

(57) ABSTRACT

An apparatus for disease prevention includes a face covering shaped to fit under a facemask of a user. The facemask fits over the nose and the mouth of the user. An ultraviolet ("UV") emitter is coupled to the face covering and the UV emitter is positioned to expose particles between the face covering and the facemask to UV light. The face covering is positioned between the UV emitter and the face of the user.

19 Claims, 15 Drawing Sheets

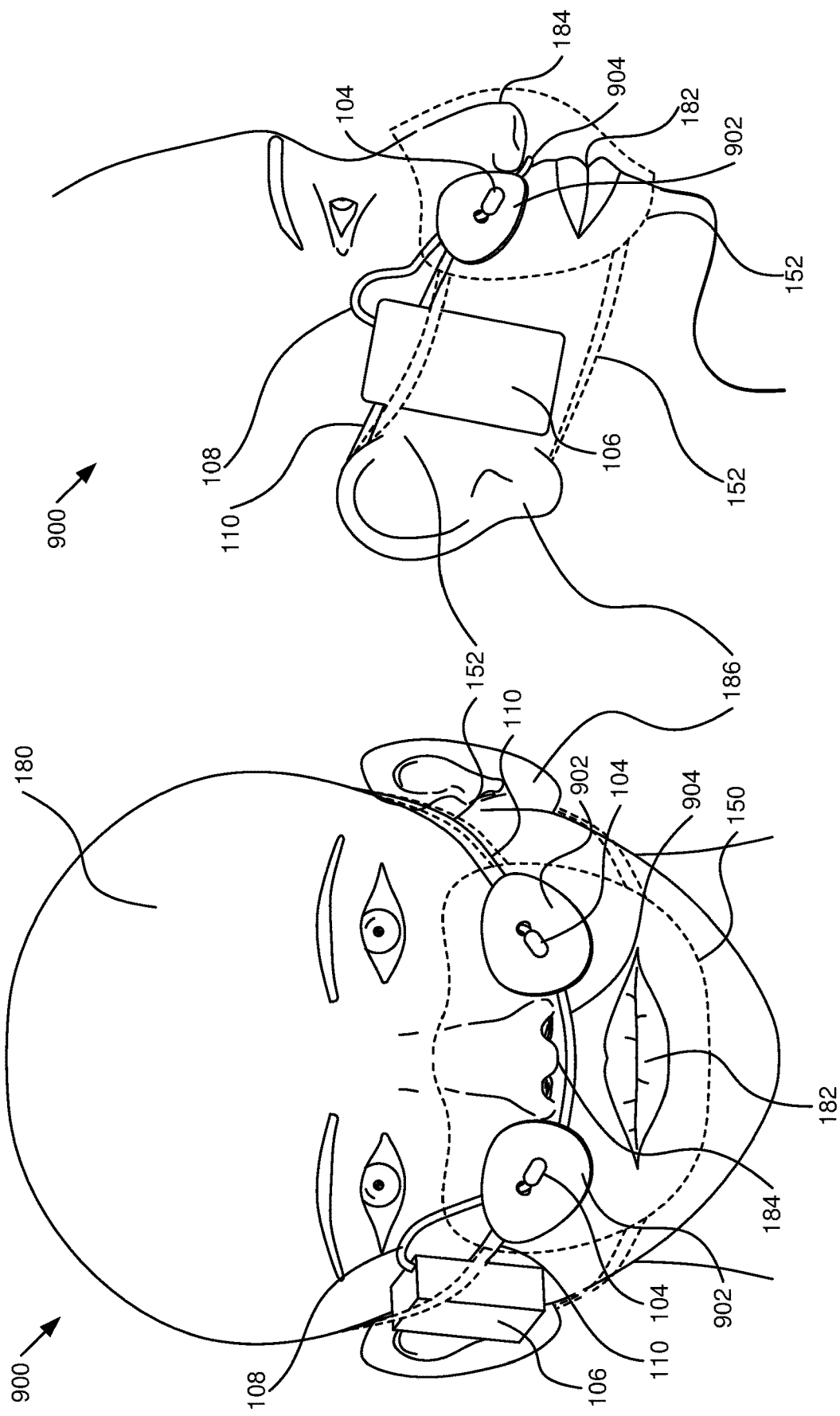

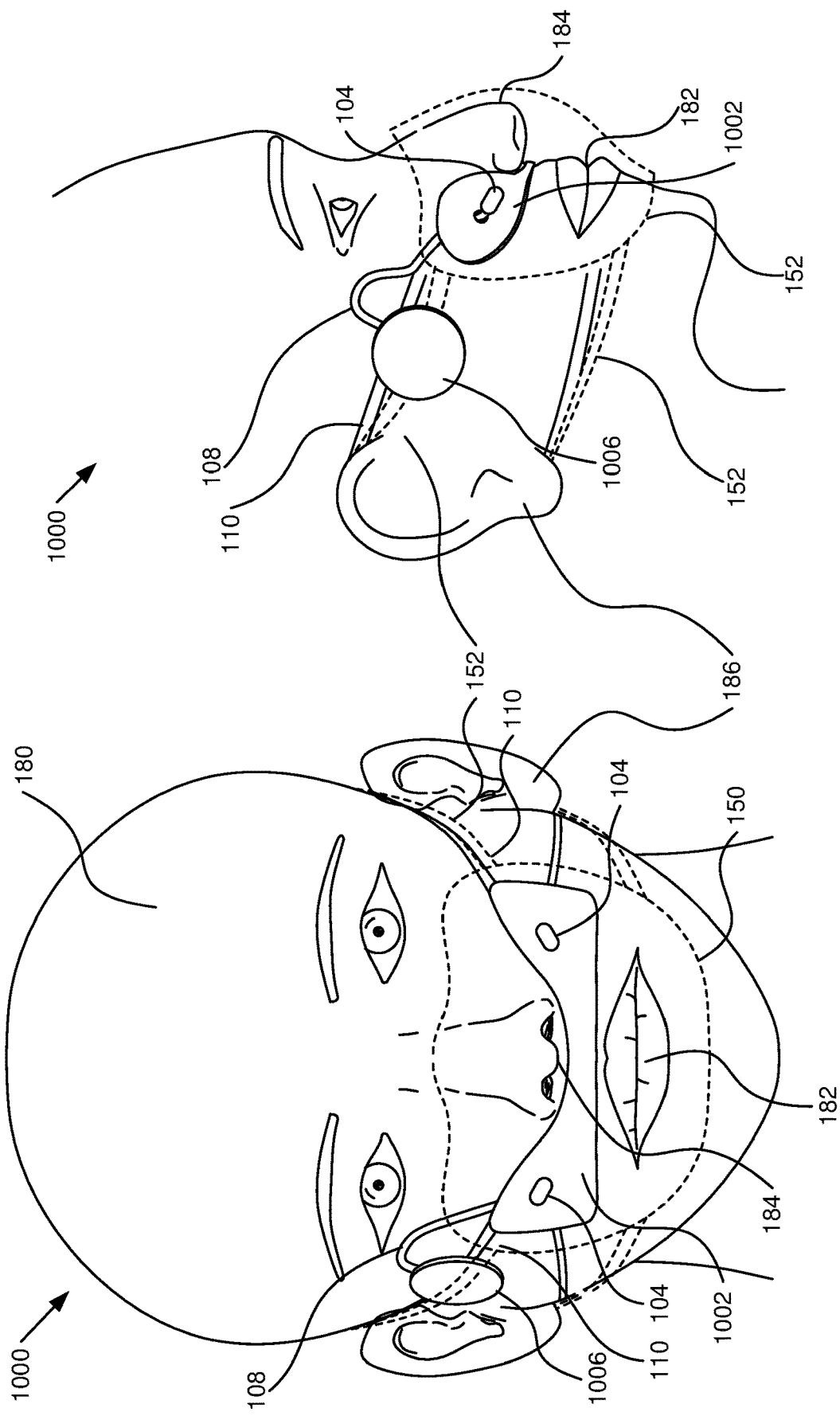

Section A-A'

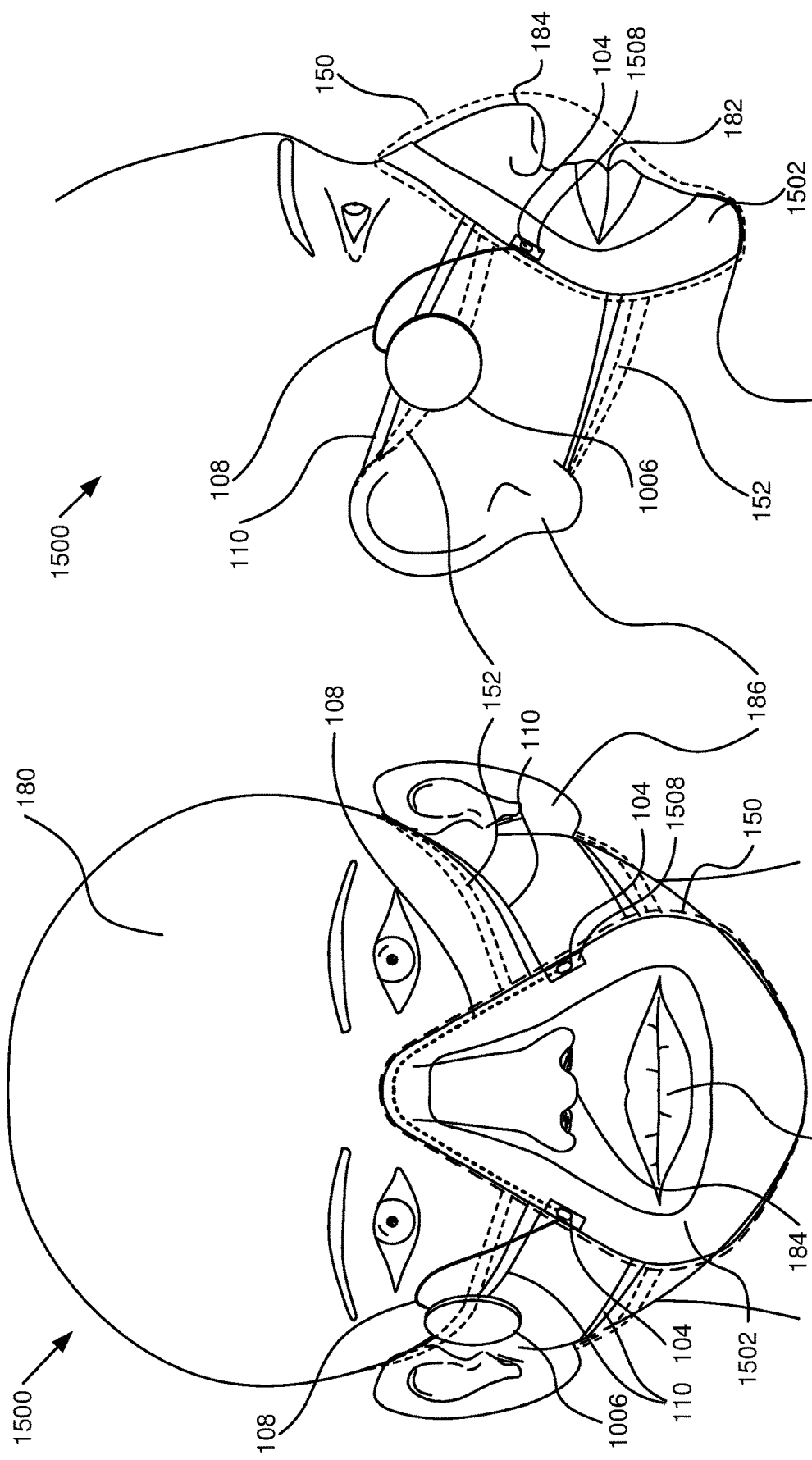

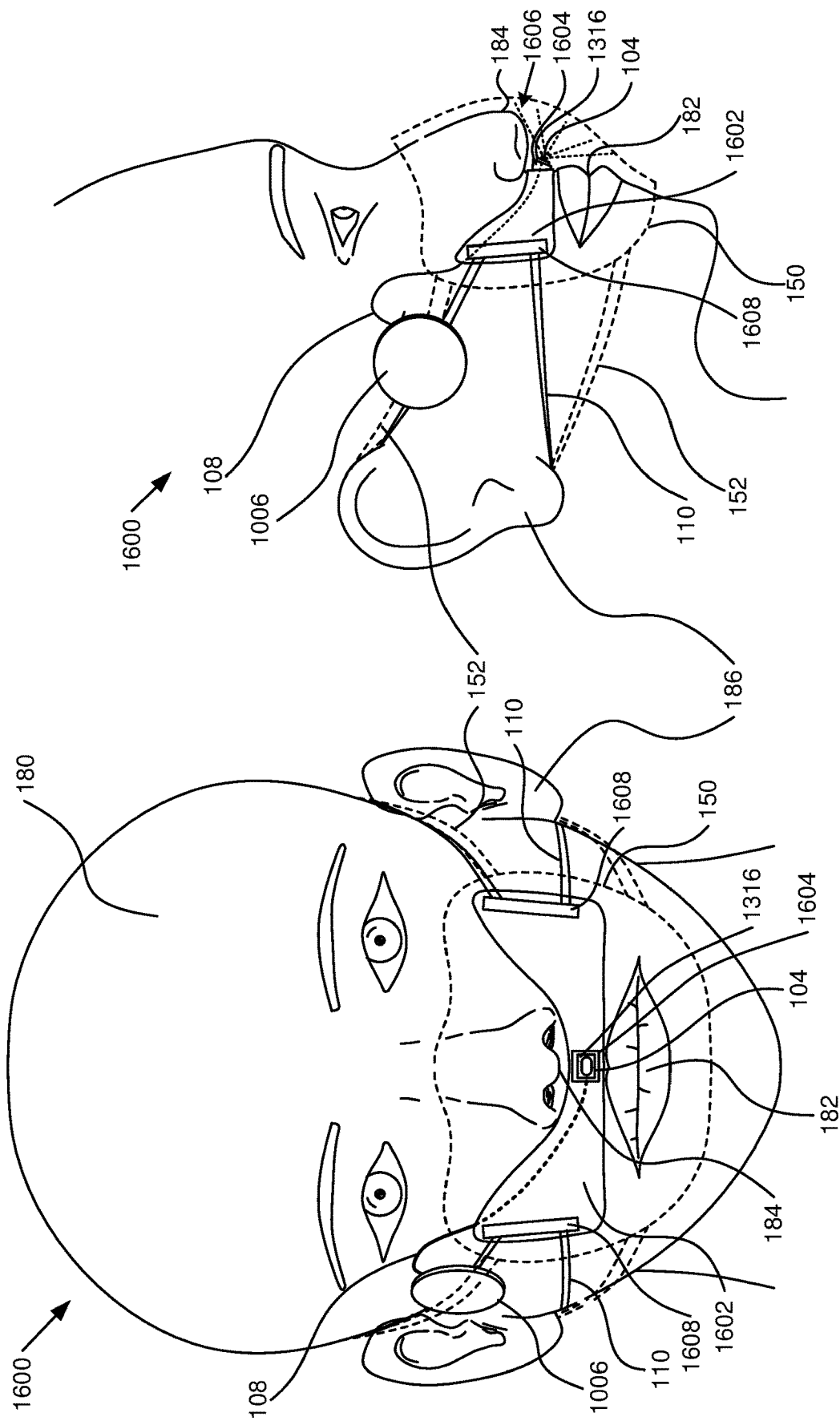

FACE COVERING WITH ULTRAVIOLET EMITTER

CROSS-REFERENCES TO RELATED APPLICATIONS

This application claims the benefit of U.S. Provisional Patent Application No. 62/983,089 entitled "FACE MASK WITH ULTRAVIOLET EMITTER" and filed on Feb. 28, 2020 for Ryan L. Babcock, et al., and U.S. Provisional Patent Application No. 63/006,839 entitled "FACE MASK WITH ULTRAVIOLET EMITTER" and filed on Apr. 8, 2020 for Ryan L. Babcock, et al., which are incorporated herein by reference.

FIELD

This invention relates to disease prevention and more particularly relates to a face covering with one or more ultraviolet emitters that fits under another facemask.

BACKGROUND

Facemasks are used to prevent the spread of bacterial and/or viral respiratory infection. People may wear facemasks to avoid becoming infected or to avoid spreading an infection to other people. Surgical masks may block large droplets such as from coughs or sneezes. Filtering facemasks or respirators may block smaller particles. For example, a respirator or dust filtering mask classified or certified by the National Institute for Occupational Safety and Health (NIOSH) in the "N95" classification may be at least 95% efficient at blocking particles of 0.3 microns when used and fitted correctly.

However, some particles such as smaller bacteria or viruses may still pass through a filtering mask to spread infection. Additionally, particle filtration depends on respirator fit. A poorly-fitting facemask will allow infectious particles in or out around the edges.

SUMMARY

An apparatus for disease prevention includes a face covering shaped to fit under a facemask of a user. The facemask fits over the nose and the mouth of the user. An ultraviolet ("UV") emitter is coupled to the face covering and the UV emitter is positioned to expose particles between the face covering and the facemask to UV light. The face covering is positioned between the UV emitter and the face of the user.

Another apparatus for disease prevention includes a face covering shaped to fit under a facemask of a user where the facemask fits over the nose and the mouth of the user. The face covering covers and area under the facemask and the face covering includes an opening corresponding to the mouth of the user and an opening corresponding to one or both nostrils of the user. The apparatus includes one or more straps connected to portions of the face covering on sides of the user's face. The one or more straps are configured to secure the face covering to the face of the user. The apparatus includes a UV emitter coupled to the face covering. The UV emitter is positioned to expose particles between the face covering and the facemask to UV light. The apparatus includes a battery case electrically connected to the UV emitter to power the UV emitter. The battery case is coupled to the one or more straps.

Another apparatus for disease prevention includes a face covering shaped to fit under a facemask of a user. The facemask fits over the nose and the mouth of the user and the face covering covers and area under the facemask. The face covering includes at least one opening corresponding to the mouth of the user and/or one or both nostrils of the user. The apparatus includes one or more straps connected to portions of the face covering on sides of the user's face. The one or more straps are configured to secure the face covering to the face of the user. A UV emitter is coupled to the face covering and the UV emitter is positioned to expose particles between the face covering and the facemask to UV light. The UV emitter emits narrow-spectrum far ultraviolet ("UV-C") light. The apparatus includes a battery case electrically connected to the UV emitter to power the UV emitter. The battery case is coupled to the one or more straps on a side of the face of the user and outside the facemask. The battery case includes a case shaped to store a 9 volt battery. The case includes terminals to electrically connect the battery to wires connected to the UV emitter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 9A is a front view illustrating an embodiment of an apparatus for disease prevention where the apparatus includes two face covering where each covers a portion of a side of the face of a user between the face and a UV emitter, and a strap between the two face coverings;

FIG. 9B is a side view illustrating the apparatus of FIG. 9A;

FIG. 10A is a front view illustrating an embodiment of an apparatus for disease prevention where the apparatus includes a face covering, where a portion of the face covering covers a portion of a right side of the face of a user and where a portion of the face covering covers a portion of a left side of the face of the user and two UV emitters and a button cell battery case;

FIG. 10B is a side view illustrating the apparatus of FIG. 10A;

FIG. 15A is a front view illustrating an embodiment of another apparatus of a face covering that surrounds the mouth and nose of a user with two UV emitters; and FIG. 15B is a side view of the embodiment of FIG. 15A;

FIG. 16A is a front view illustrating an embodiment of another apparatus of a face covering that includes a single UV emitter under the nose of a user;

FIG. 16B is a side view of the embodiment of FIG. 16A; and

DETAILED DESCRIPTION

Figure 1:
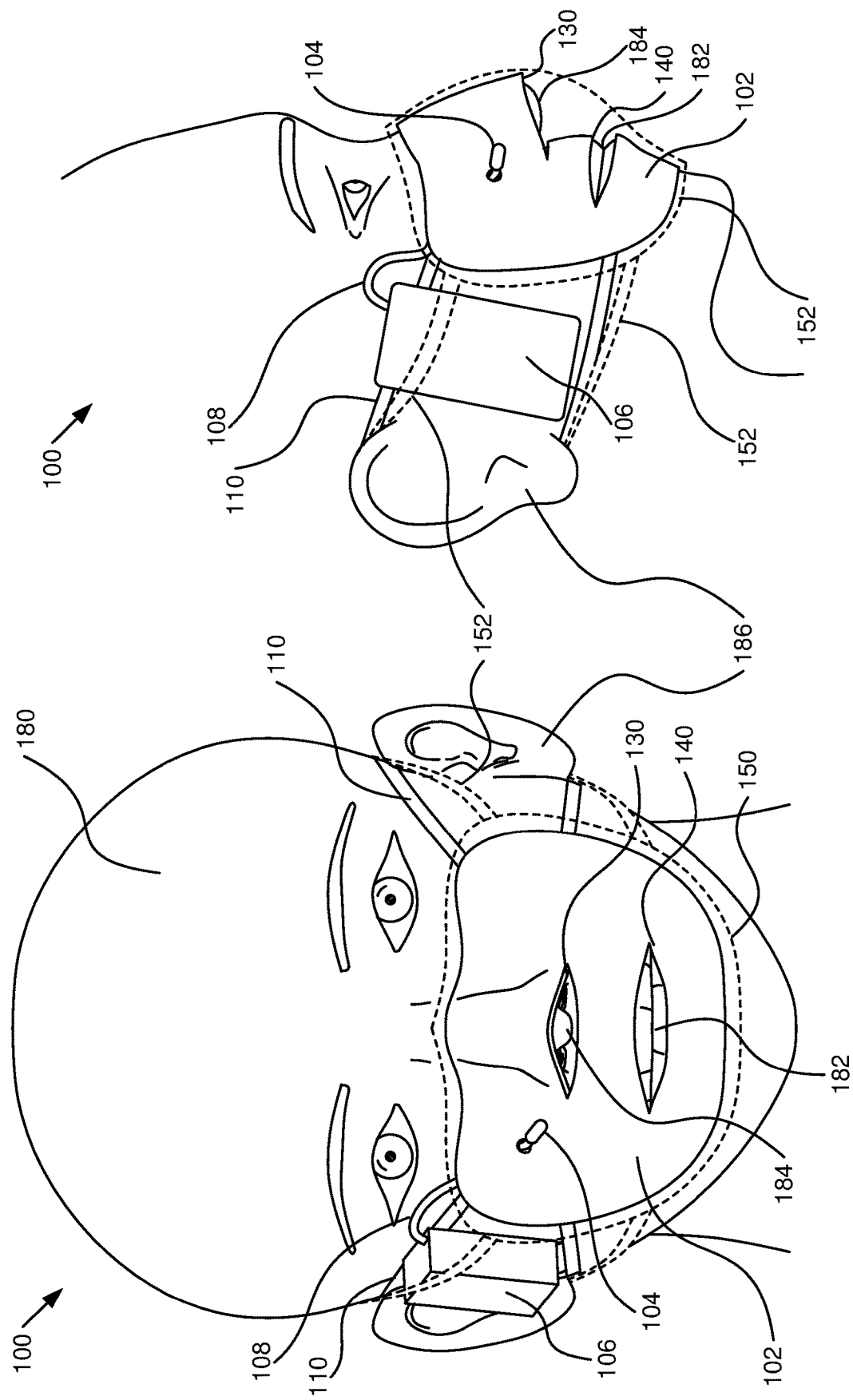
FIG. 1A is a front view illustrating an embodiment of an apparatus for disease prevention where the apparatus includes a face covering that covers the face of a user and one ultraviolet ("UV") emitter where the face covering and UV emitter are under a mask.
FIG. 1B is a side view illustrating the apparatus of FIG. 1A.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, structures, or characteristics of the invention may be combined in any suitable manner in one or more embodiments. In the following description, numerous specific details are included to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

As used herein, a list with a conjunction of "and/or" includes any single item in the list or a combination of items in the list. For example, a list of A, B and/or C includes only A, only B, only C, a combination of A and B, a combination of B and C, a combination of A and C or a combination of A, B and C. As used herein, a list using the terminology "one or more of" includes any single item in the list or a combination of items in the list. For example, one or more of A, B and C includes only A, only B, only C, a combination of A and B, a combination of B and C, a combination of A and C or a combination of A, B and C. As used herein, a list using the terminology "one of" includes one and only one of any single item in the list. For example, "one of A, B and C" includes only A, only B or only C and excludes combinations of A, B and C. As used herein, "a member selected from the group consisting of A, B, and C," includes one and only one of A, B, or C, and excludes combinations of A, B, and C." As used herein, "a member selected from the group consisting of A, B, and C and combinations thereof" includes only A, only B, only C, a combination of A and B, a combination of B and C, a combination of A and C or a combination of A, B and C.

In the following description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

An apparatus for disease prevention includes a face covering shaped to fit under a facemask of a user. The facemask fits over the nose and the mouth of the user. An ultraviolet ("UV") emitter is coupled to the face covering and the UV emitter is positioned to expose particles between the face covering and the facemask to UV light. The face covering is positioned between the UV emitter and the face of the user.

In some embodiments, the apparatus includes a battery case coupled to the UV emitter to power the UV emitter. In other embodiments, a battery case is secured to the face covering in a location that is within a volume between the face covering and the facemask. In other embodiments, the battery case includes a case shaped to hold button cell battery, a 9 volt battery and/or a 12 volt battery. In some embodiments, the battery case includes a strap shaped to secure the battery case to the user, where a wire couples the battery case to the UV emitter. In other embodiments, the apparatus includes a heat sink positioned between the UV emitter and the face covering. In other embodiments, the face covering covers an area of the face of the user under the facemask and the facemask is shaped to cover the nose and mouth of the user. In other embodiments, the face covering covers the face of the user beyond the area covered by the facemask. In other embodiments, the face covering has an opening that exposes nostrils of the user and/or an opening that exposes the mouth of the user, where UV light from the UV emitter is directed to avoid the nostrils and/or mouth of the user.

In some embodiments, the face covering includes a single UV emitter located below the nose, where a block is placed between the UV emitter and the face covering and is shaped to prevent UV light from the UV emitter from shining directly onto the nose and/or the mouth of the user. In some embodiments, material of the face covering has a nostril opening that exposes nostrils of the user and/or a mouth opening that exposes the mouth of the user, where the nostril and/or the mouth opening are covered with a mesh material. In other embodiments, the face covering covers a portion to a side of the mouth and nose of the user and is sized to prevent UV light from the UV emitter from shining directly on skin of the face of the user. In other embodiments, the UV emitter emits narrow-spectrum far ultraviolet ("UV-C") light. In other embodiments, the UV emitter further emits light in a spectrum of light visible to humans.

In some embodiments, the apparatus includes two or more UV emitters where each of the two or more UV emitters is positioned to emit light in a different portion of a volume between the face covering and the facemask. In other embodiments, the face covering includes straps attached to portions of the face coverings on sides of the user's face. The straps secure the face covering to the face of the user. In other embodiments, a battery case is secured to the straps. In other embodiments, the face covering includes a material that shields the face of the user from UV light from the UV emitter. In other embodiments, the face covering covers the nostrils and the mouth of the user, where a material covering the nostrils and the mouth of the user permits air to pass through the material. In other embodiments, the face covering covers a portion of the face of the user under the facemask and one or more UV emitters are positioned on the face covering to avoid shining UV light directly on skin of the face of the user.

Another apparatus for disease prevention includes a face covering shaped to fit under a facemask of a user where the facemask fits over the nose and the mouth of the user. The face covering covers and area under the facemask and the face covering includes an opening corresponding to the mouth of the user and an opening corresponding to one or both nostrils of the user. The apparatus includes one or more straps connected to portions of the face covering on sides of the user's face. The one or more straps are configured to secure the face covering to the face of the user. The apparatus includes a UV emitter coupled to the face covering. The UV emitter is positioned to expose particles between the face covering and the facemask to UV light. The apparatus includes a battery case electrically connected to the UV emitter to power the UV emitter. The battery case is coupled to the one or more straps.

In some embodiments, the UV emitter is a first UV emitter and the apparatus includes a second UV emitter coupled to the face covering. The second UV emitter is electrically connected to the battery case or electrically connected to a second battery case. The second battery case is coupled to the one or more straps. The UV emitter emits narrow-spectrum far ultraviolet ("UV-C") light.

Another apparatus for disease prevention includes a face covering shaped to fit under a facemask of a user. The facemask fits over the nose and the mouth of the user and the face covering covers and area under the facemask. The face covering includes at least one opening corresponding to the mouth of the user and/or one or both nostrils of the user. The apparatus includes one or more straps connected to portions of the face covering on sides of the user's face. The one or more straps are configured to secure the face covering to the face of the user. A UV emitter is coupled to the face covering and the UV emitter is positioned to expose particles between the face covering and the facemask to UV light. The UV emitter emits narrow-spectrum far ultraviolet ("UV-C") light. The apparatus includes a battery case electrically connected to the UV emitter to power the UV emitter. The battery case is coupled to the one or more straps on a side of the face of the user and outside the facemask. The battery case includes a case shaped to store a 9 volt battery. The case includes terminals to electrically connect the battery to wires connected to the UV emitter.

FIG. 1A is a front view illustrating an embodiment of an apparatus 100 for disease prevention where the apparatus 100 includes a face covering 102 that covers the face of a user 180 and one ultraviolet ("UV") emitter 104 where the face covering 102 and UV emitter 104 are under a facemask 150, and FIG. 1B is a side view illustrating the apparatus of FIG. 1A. The apparatus 100 includes a face covering 102, a UV emitter 104, a battery case 106, a wire 108, a strap 110, a facemask 150, a facemask strap 152, a user 180, a mouth 182 of the user 180, a nose 184 of the user 180 and an ear 186 of the user 180, which are described below.

The face covering 102 is positioned on the face of a user 180 and between the face of the user 180 and the facemask 150. The UV emitter 104 is positioned on the face covering 102 to be between the face of the user 180 and the facemask 150 and to emit UV light in a cavity formed between the face of the user 180 and the facemask 150. The UV emitter 104 is positioned on the face covering 102 so that direct UV light from the UV emitter 104 does not shine directly on skin of the user 180. In some embodiments, the UV emitter 104 is on a particular side of the face of the user 180 which is opposite an outlet port of a facemask 150. For example, if facemasks 150, such as N95 masks, include an outlet port for air exhausted from the facemasks 150 then placement of the UV emitter 104 may be on the right side, which may cover more air coming in through the mask than if the UV emitter 104 was placed on the same side as the exhaust port. In various embodiments, if the UV emitter 104 is on a particular side of the face of the user 180, the battery case 106 may be on the same side to minimize length of the wire 108.

Although air filtration may remove some infectious particles from the air a wearer breathes, some particles such as smaller bacteria or viruses may still pass through a filter of a facemask 150, or around the edges of a facemask 150 that does not fit the user 180 properly, or is improperly worn. However, ultraviolet light has been shown to eradicate bacteria and viruses and may eradicate bacteria and viruses that pass through or around the facemask 150 or that otherwise circumvent the filtering effects of the facemask 150 before entering the nose 184 and/or mouth 182 of the user 180.

Thus, in the depicted embodiment, the apparatus 100 includes one or more UV emitters 104. In the depicted embodiment, the apparatus 100 includes a single UV emitter 104. In another embodiment, an apparatus 100 includes multiple UV emitters 104. The UV emitters 104 may be coupled to the facemask 150, and may be configured (e.g., positioned, aimed, or the like) to expose particles to ultraviolet light inside the facemask 150.

An UV emitter 104, in various embodiments, may be any device capable of producing ultraviolet light, such as an ultraviolet light-emitting diode (LED) or another type of ultraviolet lamp. In some embodiments, an UV emitter 104 may produce germicidal ultraviolet light, such as broad-spectrum germicidal ultraviolet light with wavelengths in the 100-400 nanometer (nm) range, narrow-spectrum far ultraviolet (UV-C) light with a range of 280-100 nm wavelength, or the like. For example, the UV emitter 104 may be an LED UV emitter from American Opto Plus LED Corp. In one instance, the UV emitter 104 is model L944-UV265-2-20. In some embodiments, the UV emitter 104 may emit light in a range of about 250-275 nm. Some germicidal UV emitters are in this range. In some embodiments, the UV emitter 104 may emit light at around 265 nm. Other embodiments include other UV emitter models and/or types. Various types of germicidal ultraviolet light and UV emitters 104 capable of producing germicidal ultraviolet light, known or yet to be discovered, may be included in an apparatus 100.

When the UV emitter 104 or UV emitters 104 are powered on to emit ultraviolet light, a volume of inhaled air within the facemask 150 (or between the facemask 150 and the face of the user 180) may be exposed to ultraviolet light. In the depicted embodiment, the one or more UV emitters 104 are disposed to emit ultraviolet light between an inner surface of the facemask 150 and the face covering 102 and/or portions of the face of the user 180 not covered by the face covering 102. (The "inner" surface refers to the surface of the facemask 150 that faces towards the user 180 when the facemask 150 is worn). Additionally, particles that do not pass through the volume of direct exposure may be exposed to scattered ultraviolet light within the facemask 150, or between the facemask 150 and the face of the user 180. In some embodiments, the UV emitter 104 directs ultraviolet light in a volume around the nose 184 and mouth 182 of the user 180 so that air breathed in by the user 180 is exposed to the ultraviolet light. In other embodiments, the UV emitter 104 directs ultraviolet light toward an area where air comes into the facemask 150.

In the depicted embodiment, the apparatus 100 includes one or more wires 108 for coupling the one or more UV emitters 104 to a battery case 106 or other power source (not shown). In the depicted embodiment, the battery is a 9-volt battery, and the battery case 106 includes a 9-volt battery connector. Other embodiments include a battery case 106 for one or more batteries of a different voltage. Other embodiments include a different power source, such as a fuel cell, solar cells, or other portable power source. The power source may be alone or in combination with any other portable power source. In another embodiment, a power source may be provided integral to the UV emitter 104, and a wire 108 may be omitted from an apparatus 100. For example, an UV emitter 104 may include one or more internal button-cell batteries as a power source. In another embodiment, a power source may be a small photovoltaic panel couplable to the exterior of the facemask 150, and a power connector may be included with a connector for coupling the UV emitter 104 to the photovoltaic panel. Although a battery case 106 is disposed on the outside of the face covering 102 in the depicted embodiment, a battery case 106 and/or a power source may be disposed on the inside of the facemask 150 in another embodiment (e.g., with a more spacious facemask 150). Various other or further types of power sources and connectors for coupling power sources to UV emitters 104 may be included in or used with an apparatus 100.

In some examples, a UV emitter 104 may be an ultraviolet LED or another type of ultraviolet lamp, and may produce germicidal ultraviolet light, such as broad-spectrum germicidal ultraviolet light with wavelengths in the 200-400 nm range, narrow-spectrum far ultraviolet (UV-C) light, or other UV emitter 104 effective to kill viruses and bacteria. In some embodiments, the face covering 102 includes more than one UV emitters 104 (not shown). For example, the face covering 102 may include a UV emitter 104 on each side of the face of the user 180. In the embodiments, the multiple UV emitters 104 may be fed from a same battery case 106 or from multiple battery cases 106 (not shown).

The battery case 106, in the depicted embodiment, is coupled to the UV emitter 104 to power the UV emitter 104. In various embodiments, a battery case 106 may be any packaging that includes and/or stores a power source such as a battery, a watch battery, a coin cell, or the like, for powering a UV emitter 104. (The term "battery" may be used herein to refer to a plurality of voltaic cells or to a single voltaic cell). In some embodiments, a battery case 106 may include other or further components in addition to a battery, such as an on/off switch, a current-limiting resistor, or other electronics to regulate the voltage and/or current provided from the battery case 106 to the UV emitter 104. In some embodiments, the battery case 106 is a flat battery holder that can be opened to insert or remove a "coin cell" type battery, which may also be known as a watch battery or button cell. In other embodiments, the battery case 106 is sized for a 9-volt battery. The use of flat batteries and battery cases 106 may allow the battery case 106 to be positioned near or against a user's face without significant discomfort. Although a single battery case 106 and a single UV emitter 104 are depicted in FIGS. 1A and 1B, another embodiment of an apparatus 100 for disease prevention may include one or more UV emitters 104, coupled to and powered by one or more battery cases 106.

The face covering 102, in various embodiments, may be worn between a user's face and one or more UV emitters 104. In various embodiments, a face covering 102 may be worn under a facemask 150, which may be filtration mask such as NIOSH-approved mask with at least an N95 filtration rating or other paper facemask, cloth facemask, etc. The facemask 150 and facemask straps 152 are depicted as dashed lines in FIGS. 1A and 1B, to depict the fit of the face covering 102 under the facemask 150. In various embodiments, a conventional or commercially available outer facemask 150 may be worn for filtration, and the inner face covering 102 may be worn to shield the user's face from the ultraviolet light emitted by the UV emitter(s) 104. Thus, in some embodiments, the face covering 102 may be made of a material that is opaque to the ultraviolet light emitted by the UV emitter(s) 104, or that significantly attenuates the ultraviolet light. In one embodiment, the face covering 102 may be made of neoprene (e.g., 2 mm neoprene) or another elastic, flexible material. In another embodiment, the face covering 102 may be made of cloth. In some embodiments the face covering 102 may include two layers, to conceal leads (e.g. wire 108) for the UV emitter(s) 104 between layers.

In some embodiments, the apparatus 100 is reusable, and may be worn multiple times under different (or reused) outer facemasks 150. For example, if an outer facemask 150 has reached its filtration capacity, become damaged, or otherwise needs to be replaced, the apparatus 100 may continue to be used with a new outer facemask 150. Additionally, although the apparatus 100 has been described herein for use with a conventional or commercially available outer facemask 150, the apparatus 100 may also be used with an improvised or homemade outer facemask 150. Such a facemask 150 may include a porous and flexible filtration material (e.g., cloth from bandannas, scarves, pillowcases, tee shirts, or the like, or paper filtration material such as coffee filters), which may be worn over a user's mouth 182 and nose 184 to allow inhaled air to flow through the filtration material. An apparatus 100 for disease prevention may be worn under the outer facemask 150 (whether commercially available or improvised) to expose particles between the face covering 102 and the outer facemask 150 to ultraviolet light from the UV emitter(s) 104.

The face covering 102, in the depicted embodiment, includes a nostril slit 130. The nostril slit 130 is formed to be positioned under a user's nose 184, to facilitate comfortable breathing, and/or to conform more comfortably to the user's nose 184 and upper lip. In other embodiments, the face covering 102 includes a mouth slit 140 to expose the lips and mouth 182 of the user 180. In another embodiment, the face covering 102 may be formed of a breathable material, and a nostril slit 130 and mouth slit 140 may be omitted.

The one or more UV emitters 104 are coupled to the face covering 102 to expose particles (e.g., infectious viruses) between the face covering 102 and an outer facemask 150 to ultraviolet light. In the depicted embodiment, the face covering 102 does not cover the user's mouth 182 or nostrils, so some of the user's skin within the outline of the outer facemask 150 may be exposed to ultraviolet light from the UV emitter(s) 104. For example, skin within the outline of the outer facemask 150 may be exposed to light scattered off an inner surface of the outer facemask 150. However, the risk of skin exposure to attenuated, scattered ultraviolet light may be less than the risk of direct exposure (e.g., without a face covering 102). In some embodiments, the face covering 102 may be shaped to protect a user's face from ultraviolet light in areas that are proximate to or directly behind an UV emitter 104. Conversely, in some embodiments, the face covering 102 may be shaped to cover substantially all of a user's skin behind an outer facemask 150. For example, the face covering 102 may have the same outline as the outer facemask 150.

In the depicted embodiment, straps 110 that form ear loops are coupled to the face covering 102. The straps 110 may be similar to ear loops for a surgical mask, a filtration mask, or the like, and may be made of cloth, elastic, or the like, so that the face covering 102 is positioned in front of a user's face by securing the straps 110 around the user's ears 186. In other embodiments, the straps 110 extend around the head and/or neck of the user 180. The straps 110 may be elastic, may include clips or other hardware so the straps 110 are adjustable, etc. to the face covering 102 conforms to the face of the user 180 without slipping. For example, the straps may be tied, secured with hook and loop material, etc.

In the depicted embodiment, a battery case 106 is secured to one of the straps 110 outside the outline of the outer facemask 150. Securing battery cases 106 to ear loops may keep wires 108 from the battery cases 106 to the UV emitters 104 short, and may position the battery cases 106 to be comfortably worn and easily accessed (e.g., if a battery case 106 includes an on/off switch for a UV emitter 104). For example, the straps may be tied, secured with hook and loop material, etc.

Figure 2:
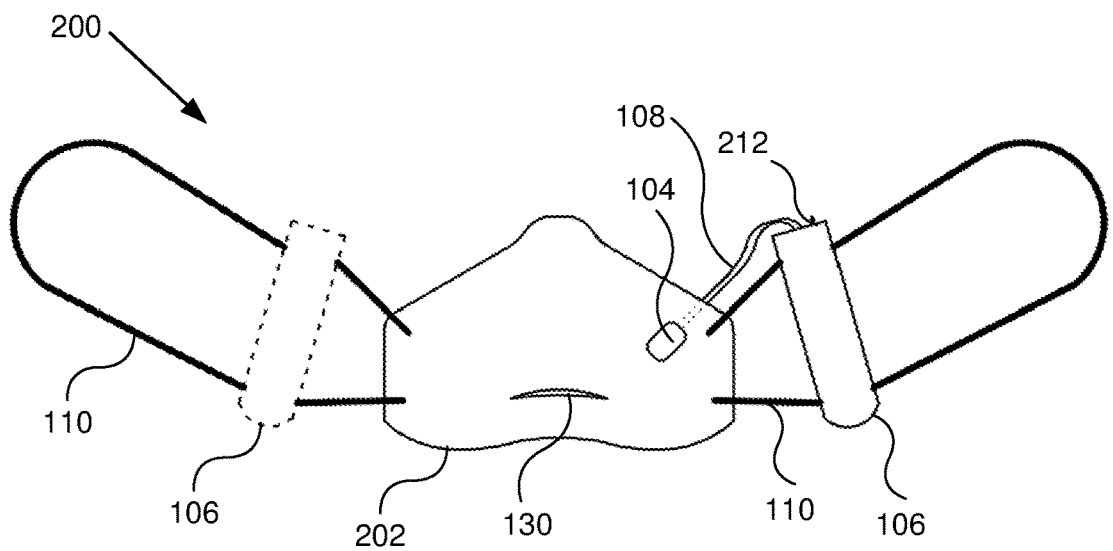
FIG. 2 is a front view illustrating another embodiment of an apparatus for disease prevention where the apparatus includes a face covering that covers the face of a user and one ultraviolet ("UV") emitter.

FIG. 2 is a front view further illustrating another apparatus 200 similar to the apparatus 100 of FIG. 9. In the depicted embodiment, the apparatus 100 includes a face covering 102 that does not cover the mouth 182 of the user 180 and includes a nostril slit 130, one or more UV emitters 104, one or more battery cases 106, and straps 110, substantially as described above. In the depicted embodiments, one of the battery cases 106 indicated by a dashed line is optional, and may be included or omitted. Similarly, although a single UV emitter 104 is detected, a second UV emitter 104 (not shown) may be optionally included, powered by the optional second battery case 106. In another embodiment, a second battery case 106 may power a single UV emitter 104 alongside the first battery case 106 for longer-duration use. In the depicted embodiment, one or both battery cases 106 may include an on/off switch 212. The switch 212 may allow a user to switch the UV emitter(s) 104 on when putting on the apparatus 200 and an outer facemask 150, and to switch the UV emitter(s) 104 off when no longer needed.

Figure 3:
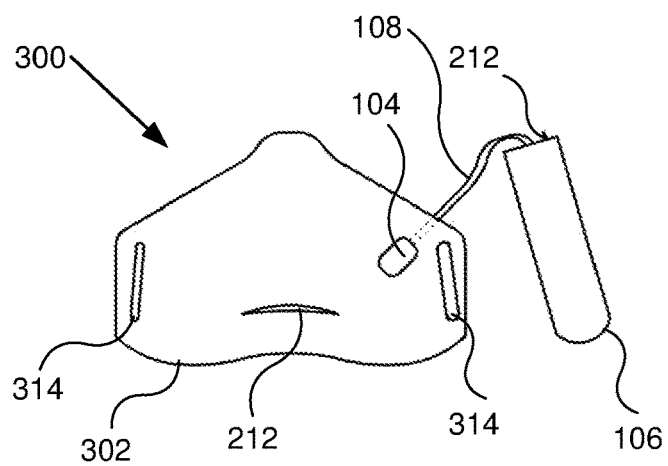
FIG. 3 is a front view illustrating another embodiment of an apparatus for disease prevention with slots for straps.

FIG. 3 is a front view illustrating another embodiment of an apparatus 300 for disease prevention. The apparatus 300, in various embodiments, may be substantially similar to the apparatuses 100, 200 described above with reference to FIGS. 1A, 1B and 2, including a face covering 302 with a nostril slit 130, one or more ultraviolet emitters 1108, one or more battery cases 106, and an on/off switch 212, substantially as described above. However, the apparatus 300 does not include ear loops. Instead, the face covering 302 includes side openings 314 at the left and right sides of the face covering 302. Ear loops for an outer facemask 150 may be passed through the side openings 314 to position the face covering 302 underneath the outer facemask 150. The use of side openings 314 may allow a user to wear both the apparatus 100 and an outer facemask 150 with a single ear loop per ear instead of with two ear loops on each ear.

Figure 4:
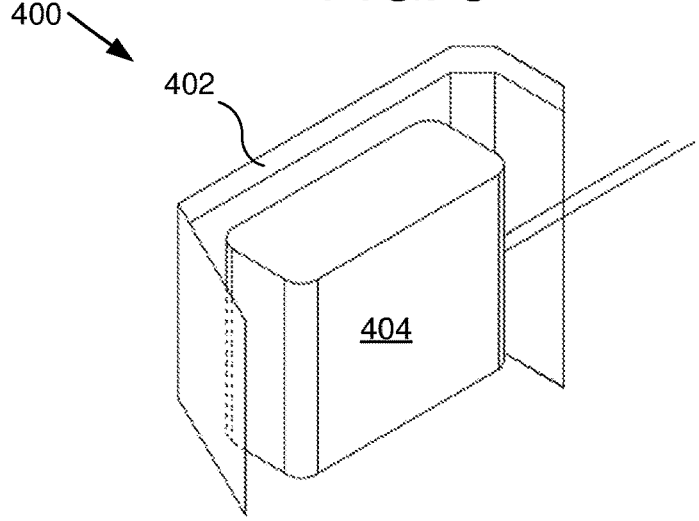
FIG. 4 is a perspective view illustrating one embodiment of a shielded ultraviolet emitter.

FIG. 4 is a perspective view illustrating one embodiment of a shielded ultraviolet emitter 400. The shielded ultraviolet emitter 400 may be used in various embodiments of apparatuses for disease prevention as described herein. In the depicted embodiment, the shielded ultraviolet emitter 400 includes an ultraviolet emitter 404 and a deflector shield 402. The ultraviolet emitter 404 may be substantially similar to other ultraviolet emitters described above such as the UV emitters 104 of FIG. 1. In the depicted embodiment, the ultraviolet emitter 404 may emit ultraviolet light in multiple directions. For example, an ultraviolet LED may have some directional variation in emission, but may generally emit ultraviolet light out the end and sides of the LED package. Thus, in the depicted embodiment, a deflector shield 402 is attached to one side of the ultraviolet emitter 404 to direct the ultraviolet light away from a user's face.

The deflector shield may be made of opaque material or reflective material. When a shielded ultraviolet emitter 400 is used in an apparatus for disease prevention, the deflector shield 402 may be positioned between the ultraviolet emitter 404 and the user's face. The deflector shield 402, in various embodiments, is customized for a particular location on a face covering 102 (or other face covering 202, 302, 502, 602, 702, 802, 902, 1002, 1102, 1202, 1302 described herein) to emit UV light in a direction to avoid direct UV light on skin of the user 180 while emitting UV light in a direction to cover a volume in front of the mouth 182 and nose 184 of the user 180.

Figure 5:
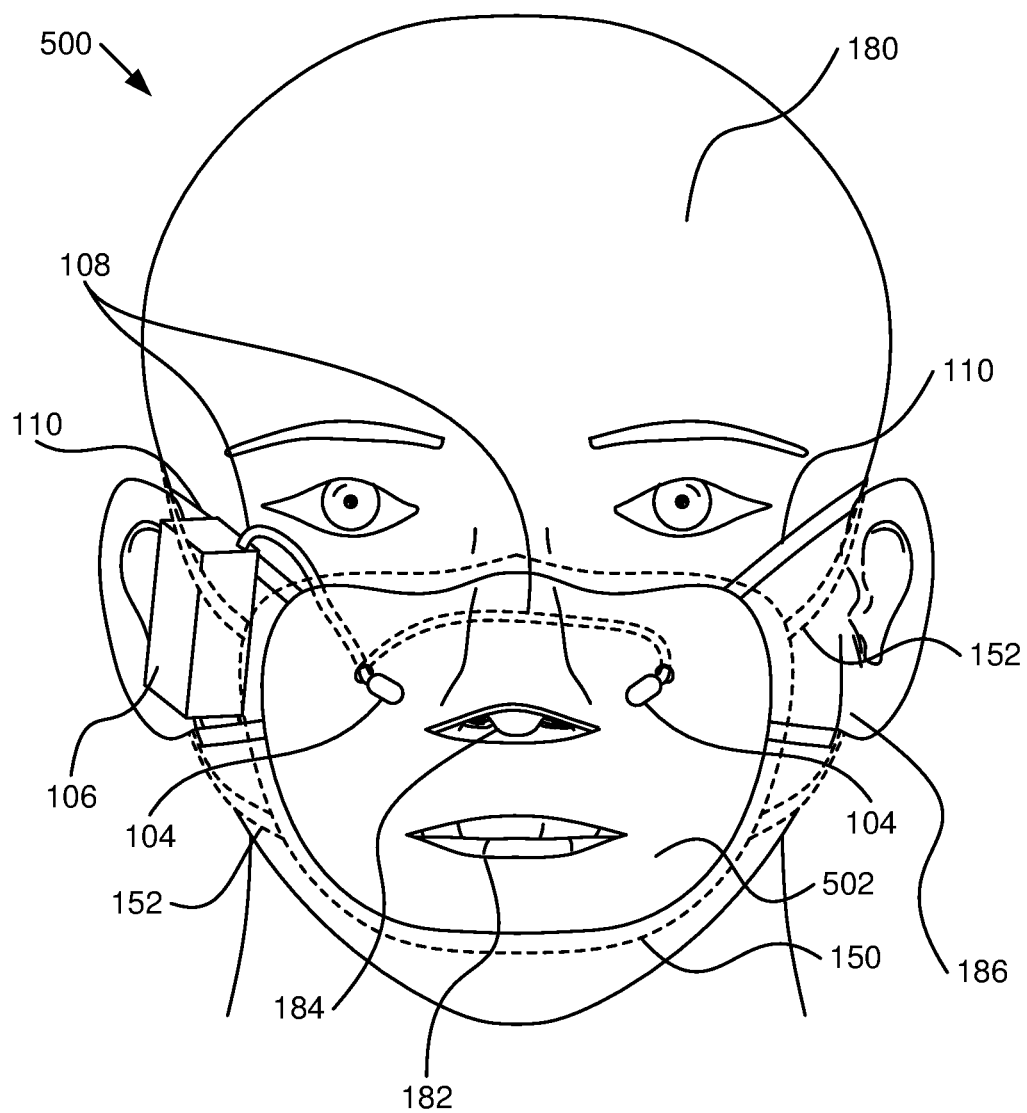
FIG. 5 is a front view illustrating an embodiment of an apparatus for disease prevention where the apparatus includes a face covering that covers the face of a user and two UV emitters.

FIG. 5 is a front view illustrating an embodiment of an apparatus 500 for disease prevention where the apparatus 500 includes a face covering 502 that covers the face of a user 180 and two UV emitters 104. The apparatus 500 is substantially similar to the apparatus 100 of FIGS. 1A and 1B but includes a second UV emitter 104 and the face covering 502 extends beyond edges of the facemask 150. In the depicted embodiment, both UV emitters 104 are powered by a single battery case 106. In other embodiments, the apparatus 500 includes a second battery case 106, which may be placed on an side opposite the first battery case 106. The face covering 502 covers a larger area than the face covering 103 of the apparatus 100 of FIGS. 1A and 1B, which may be useful to protect the face of the user 180 from UV light and from edges of the facemask 150.

In some embodiments, the battery case(s) 106 is/are connected to the straps 110. In other embodiments, the battery cases 106 are located elsewhere, such as on the face covering 502, in a pocket of the user 180, on a strap around the neck of the user 180, or the like.

Figure 6:
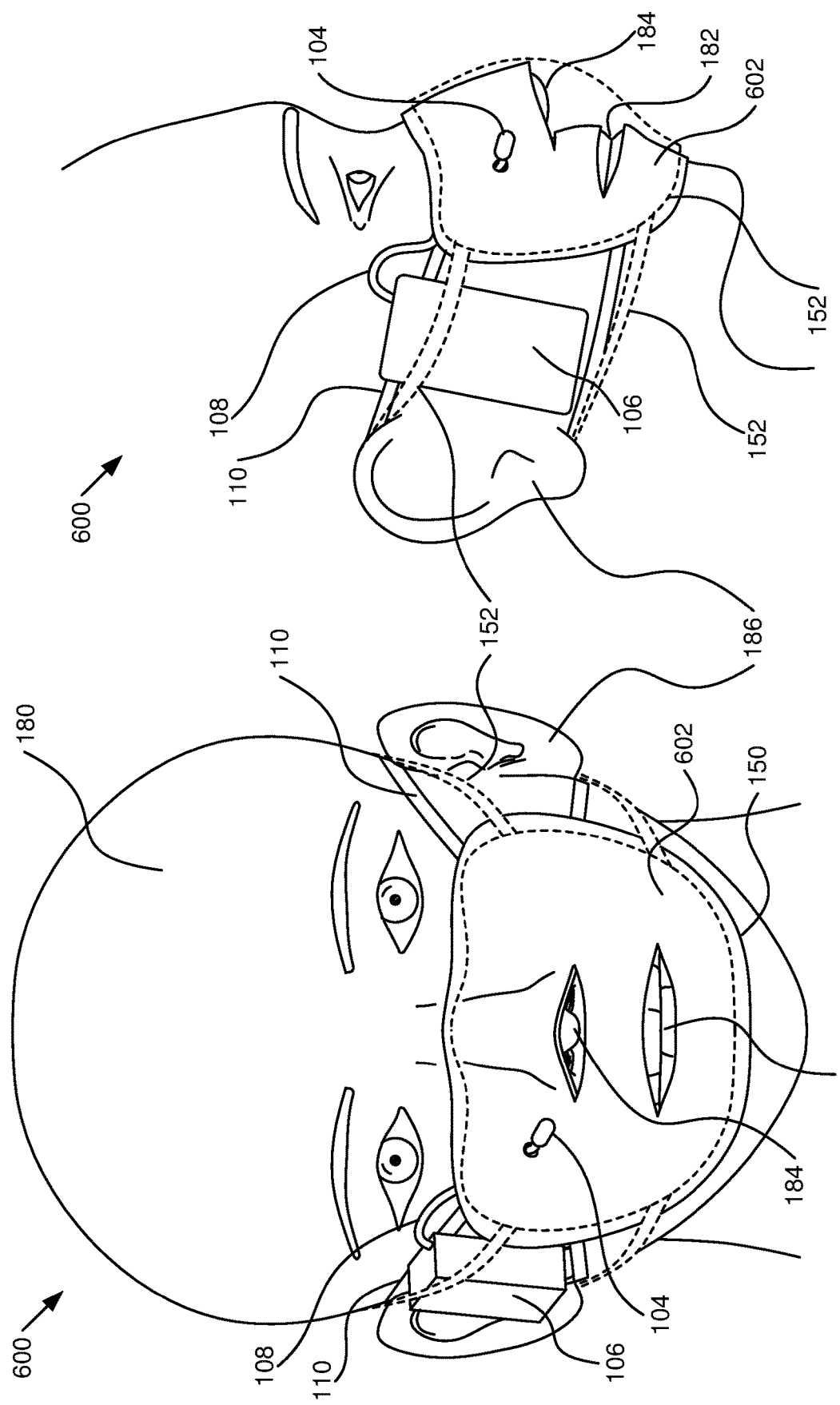
FIG. 6A is a front view illustrating an embodiment of an apparatus for disease prevention where the apparatus includes a face covering that covers the face of a user and extends beyond edges of the facemask and one UV emitter.
FIG. 6B is a side view illustrating the apparatus of FIG. 6A.

FIG. 6A is a front view illustrating an embodiment of an apparatus 600 for disease prevention where the apparatus 600 includes a face covering 602 that covers the face of a user 180 and extends beyond edges of the facemask 150 and one UV emitter 104 and FIG. 6B is a side view illustrating the apparatus 600 of FIG. 6A. The apparatus 600 is substantially similar to the apparatus 100 of FIGS. 1A and 1B except that the face covering 602 extends beyond the edges of the facemask 150.

Figure 7:
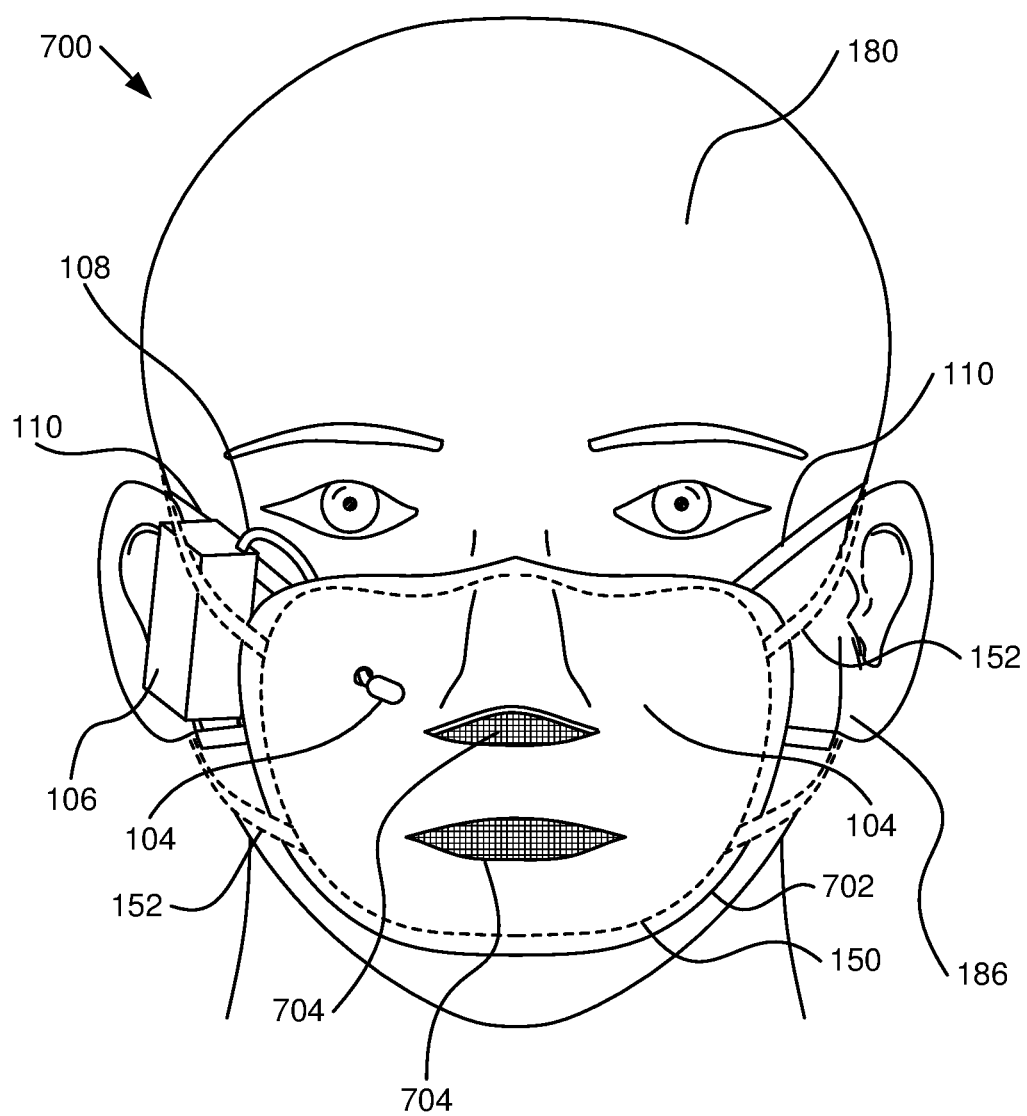
FIG. 7 is a front view illustrating an embodiment of an apparatus for disease prevention where the apparatus includes a face covering that covers the face of a user and extends beyond edges of the facemask and one UV emitter and mesh over the nose and mouth of the user.

FIG. 7 is a front view illustrating an embodiment of an apparatus 700 for disease prevention where the apparatus 700 includes a face covering 792 that covers the face of a user 180 and extends beyond edges of the facemask 150 and one UV emitter 104 and mesh 704 over the nose 184 and mouth 182 of the user 180. The apparatus 700 is substantially similar to the apparatus 600 of FIGS. 6A and 6B, but includes mesh 704 on the face covering 702 over a nose slit 130 and a mouth slit 140 for easier breathing while providing some protection from UV light on the nose 184 and mouth 182 of the user 180.

Figures 8A, 8B:
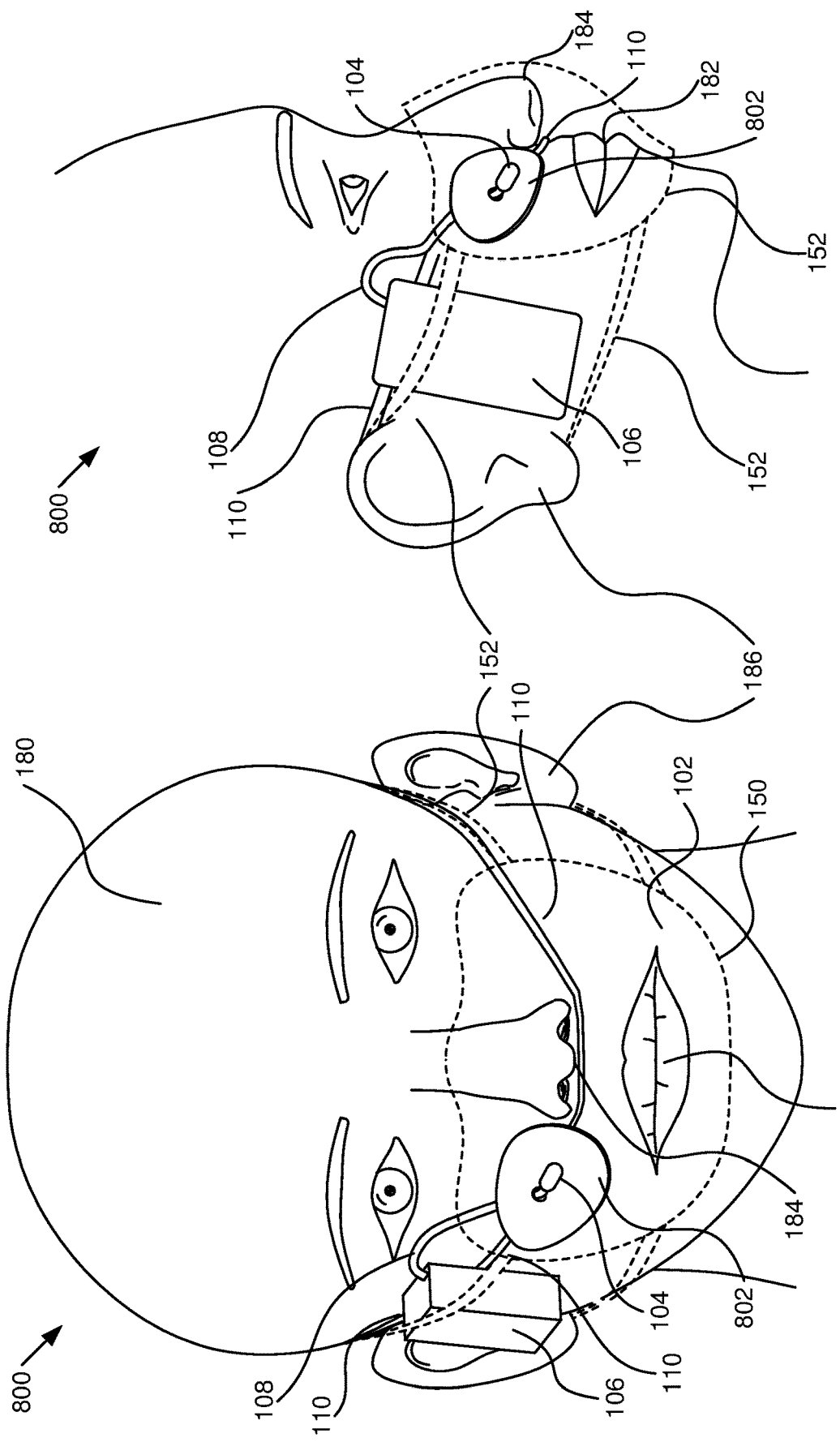
FIG. 8A is a front view illustrating an embodiment of an apparatus for disease prevention where the apparatus includes a face covering that covers a portion of a side of the face of a user between the face and a UV emitter.
FIG. 8B is a side view illustrating the apparatus of FIG. 8A.

FIG. 8A is a front view illustrating an embodiment of an apparatus 800 for disease prevention where the apparatus 800 includes a face covering 802 that covers a portion of a side of the face of a user 180 between the face and a UV emitter 104 and FIG. 8B is a side view illustrating the apparatus 800 of FIG. 8A. The face covering 802 is positioned on a cheek of the user 180 and includes straps 110 to hold the face covering 802 to the cheek of the user 180. In the depicted embodiment, the apparatus 800 includes a single strap 110 on each side and extends around the head of the user 180. In other embodiments, the straps 110 are configured as ear loops. In some embodiments, the UV emitter 104 is a UV emitter 404 with a deflector shield 402 as depicted in the UV emitter 400 of FIG. 4. In other embodiments, the UV emitter 104 and face covering 802 are shaped so direct UV light of the UV emitter 104 is not directed at skin of the user 180.

FIG. 9A is a front view illustrating an embodiment of an apparatus 900 for disease prevention where the apparatus 900 includes two face coverings 902 where each covers a portion of a side of the face of a user 180 between the face and a UV emitter 104, and a connector 904 between the two face coverings and FIG. 9B is a side view illustrating the apparatus of FIG. 9A. The apparatus 900 is substantially similar to the apparatus 800 of FIGS. 8A and 8B except with two face coverings 902.

In some embodiments, the connector 904 is a strap 110 like other straps 110 discussed herein. In other embodiments, the connector 904 includes a wire between the UV emitters 104. In other embodiments, the apparatus 900 includes a second battery case 106 (not shown). One of skill in the art will recognize other configurations of partial face coverings 902 with one or more UV emitters 104. For example, two or more UV emitters 104 may be included on each side of the face of the user 180 on the face coverings 902 of FIGS. 9A and 9B or other apparatuses 100, 200, 300, 500, 600, 700, 800, 1000, 1100, 1200, 1300 described herein. The two or more UV emitters 104 may be together or distributed on the sides of the user's face. In other embodiments, the connector 904 extends over the bridge of the nose 184 of the user 180. In other embodiments, the apparatus 900 includes two or more connectors 904.

FIG. 10A is a front view illustrating an embodiment of an apparatus 1000 for disease prevention where the apparatus 1000 includes a face covering 1002, where a portion of the face covering 1002 covers a portion of a right side of the face of a user 180 and where a portion of the face covering 1002 covers a portion of a left side of the face of the user 180 and two UV emitters 104 and a button cell battery case 1006. FIG. 10B is a side view illustrating the apparatus 1000 of FIG. 10A.

The apparatus 1000 is substantially similar to the apparatus 900 of FIGS. 9A and 9B except that the connector 904 of the apparatus 900 of FIGS. 9A and 9B is replaced by a portion of face covering 1002. The portion of face covering 1002 under the nose 184, in some embodiments, includes wiring between UV emitters 104. Having face covering material instead of a connector 904 may be beneficial for comfort of the user 180. In other embodiments, the face covering material may run over the bridge of the nose 184 of the user 180.

In the depicted embodiments, the apparatus 1000 includes a button cell battery case 1006 that holds one or more button cell batteries. Button cell batteries may be beneficial due to their size and shape. In other embodiments, the apparatus 1000 includes two or more button cell battery cases 1006. Other embodiments described herein may also include one or more button cell battery cases 1006.

Figures 11A, 11B:
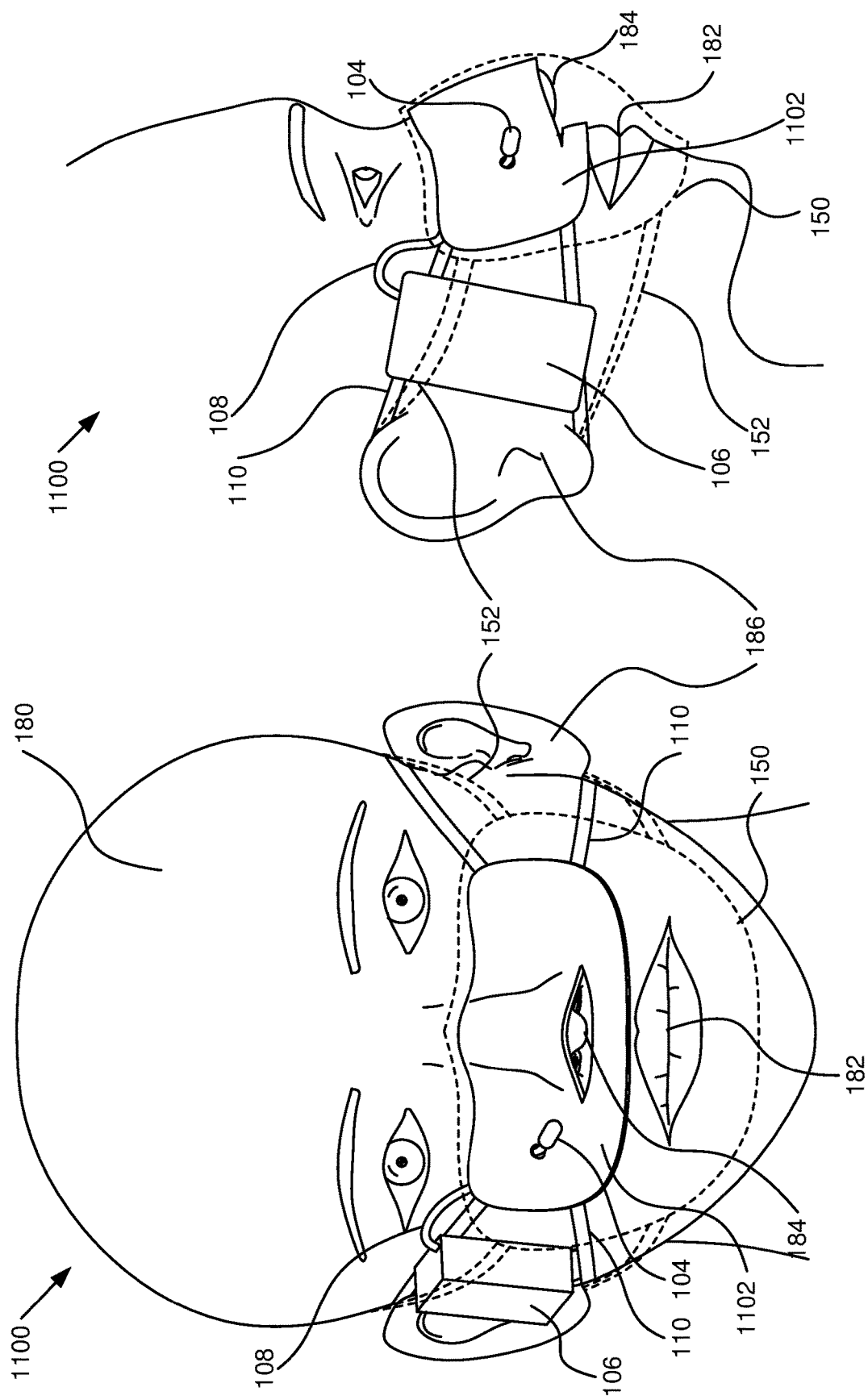
FIG. 11A is a front view illustrating an embodiment of an apparatus for disease prevention where the apparatus includes a face covering, where a portion of the face covering covers a portion of a right side of the face of a user and where a portion of the face covering covers a portion of a left side of the face and a portion covers the nose of the user and two UV emitters.
FIG. 11B is a side view illustrating the apparatus of FIG. 11A.

FIG. 11A is a front view illustrating an embodiment of an apparatus 1100 for disease prevention where the apparatus 1100 includes a face covering 1102, where a portion of the face covering 1102 covers a portion of a right side of the face of a user 180 and where a portion of the face covering 1102 covers a portion of a left side of the face and a portion covers the nose 184 of the user 180 and two UV emitters 104. FIG. 11B is a side view illustrating the apparatus of FIG. 11A. The apparatus 1100 is substantially similar to other apparatuses 100, 200, 300, 500, 600, 700, 800, 900, 1000 described herein, but has a face covering 1102 that does not cover the mouth 182 of the user 180. Other embodiments include more than one UV emitter 104, more than one battery case 106, which may be of various types and other variations.

Figure 12:
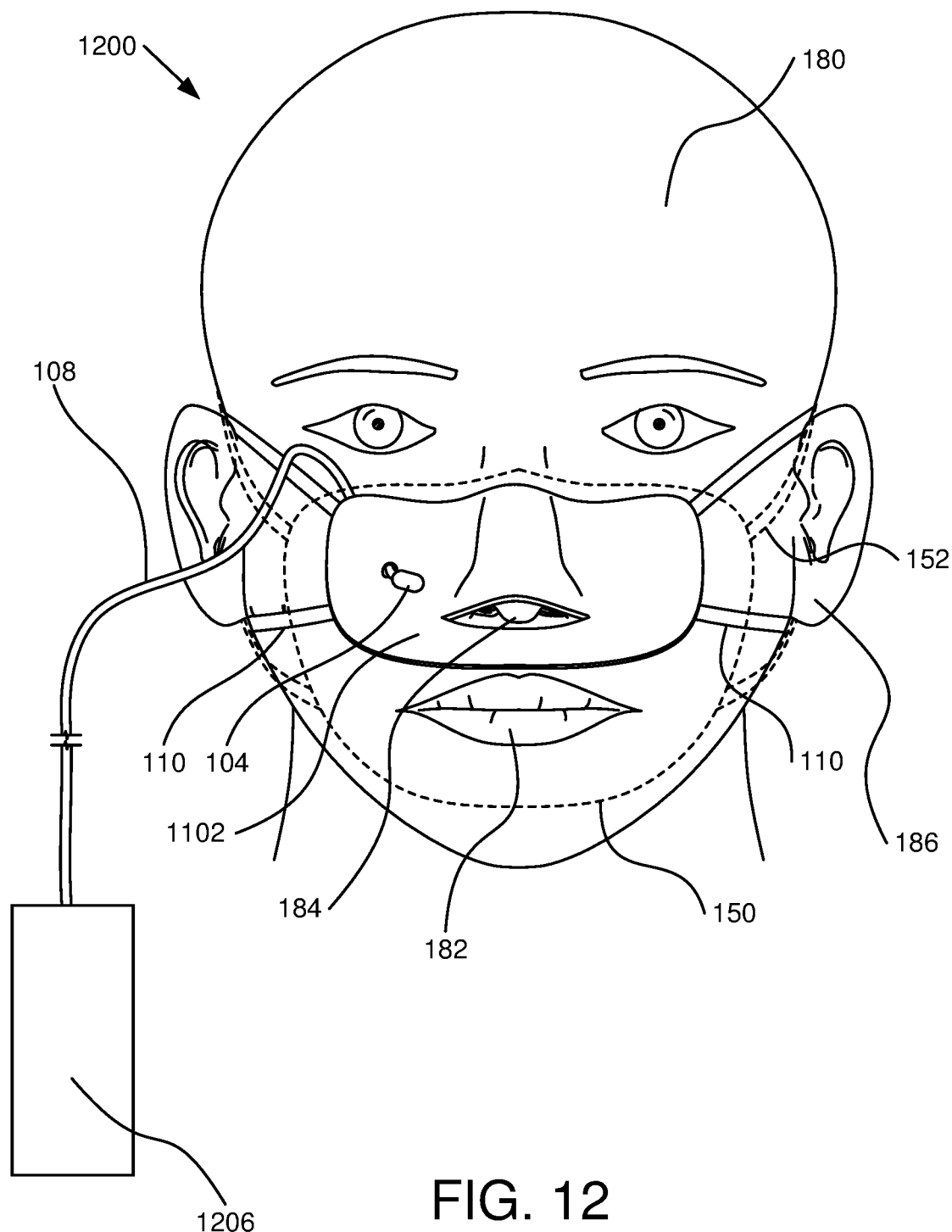
FIG. 12 is a front view illustrating an embodiment of an apparatus for disease prevention with a face covering similar to FIG. 11A and a battery case attached to the user separately from the face covering.

FIG. 12 is a front view illustrating an embodiment of an apparatus 1200 for disease prevention with a face covering 1102 similar to FIG. 11A and a battery case 1206 attached to the user 180 separately from the face covering 1102. For example, the battery case 1206 may be for a 12 volt battery and may attach to the user's belt, to a strap to be worn over the shoulder or around the neck of the user 180, etc. In various embodiments, the wire 108 is long enough to support various configurations of connection to the user 180.

Figure 13A:
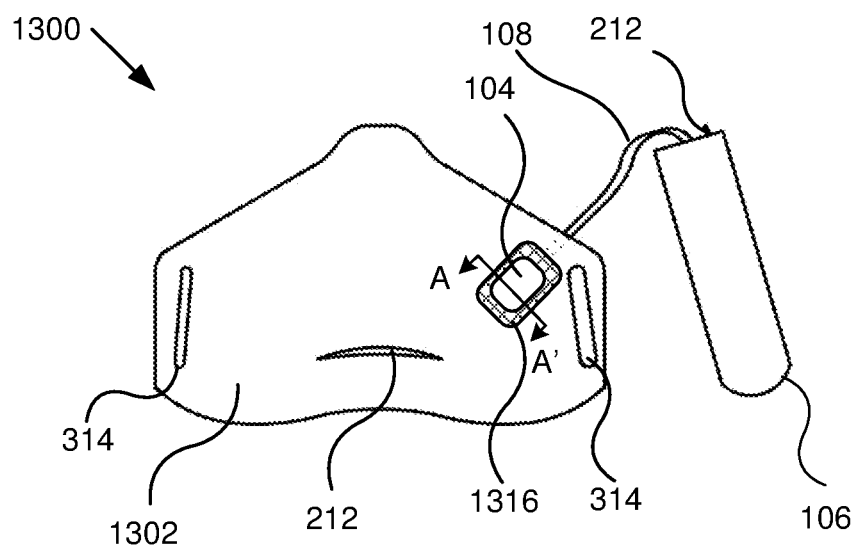
FIG. 13A is a front view illustrating a face covering with a UV emitter and a heat sink between the face covering and the UV emitter.
Figure 13B:
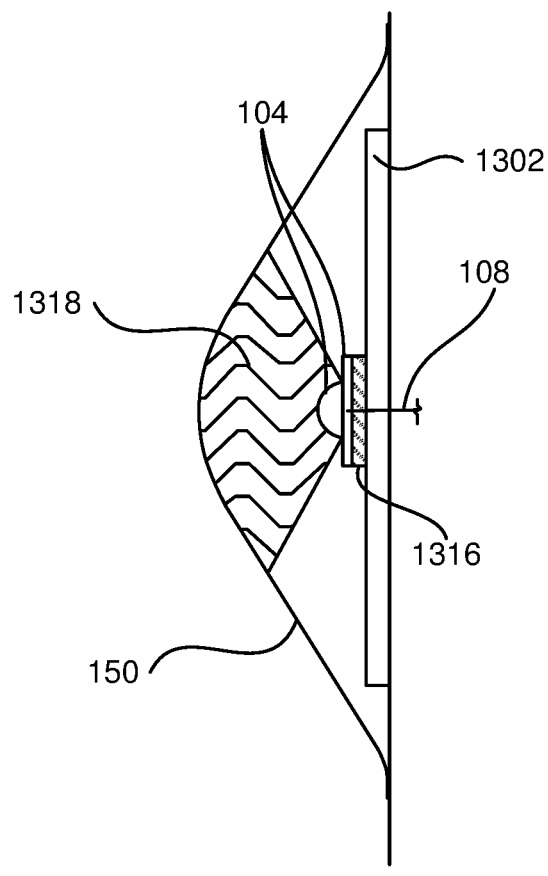
FIG. 13B is a section view of the embodiment of FIG. 13A.

FIG. 13A is a front view illustrating one embodiment of an apparatus 1300 with a face covering 1302 with a UV emitter 104 and a heat sink 1316 between the face covering and the UV emitter 104 and FIG. 13B is a section view of the embodiment of FIG. 13A. In the embodiment, the face covering 1302 is similar to the face covering 302 of FIG. 3 with openings 314 for facemask straps 152 of the facemask 150.

The heat sink 1316 is configured to prevent the UV emitter 104 from becoming uncomfortably hot for the face of the user 180. In addition, the heat sink 1316 provides shielding to direct UV light 1318 away from the skin of the user 180. In FIG. 13B, UV light 1318 from the UV emitter 104 is directed toward the inner surface of the facemask 150. The heat sink 1316 may be copper, aluminum or other suitable material and may include various layers. For example, a layer of the heat sink 1316 closest to the face covering 1302 may be a material that does not conduct heat efficiently while another layer closest to the UV emitter 104 may include a material that conducts and radiates heat. One of skill in the art will recognize other ways to configure the heat sink 1316 to protect the face of the user 180.

Figures 14A, 14B:
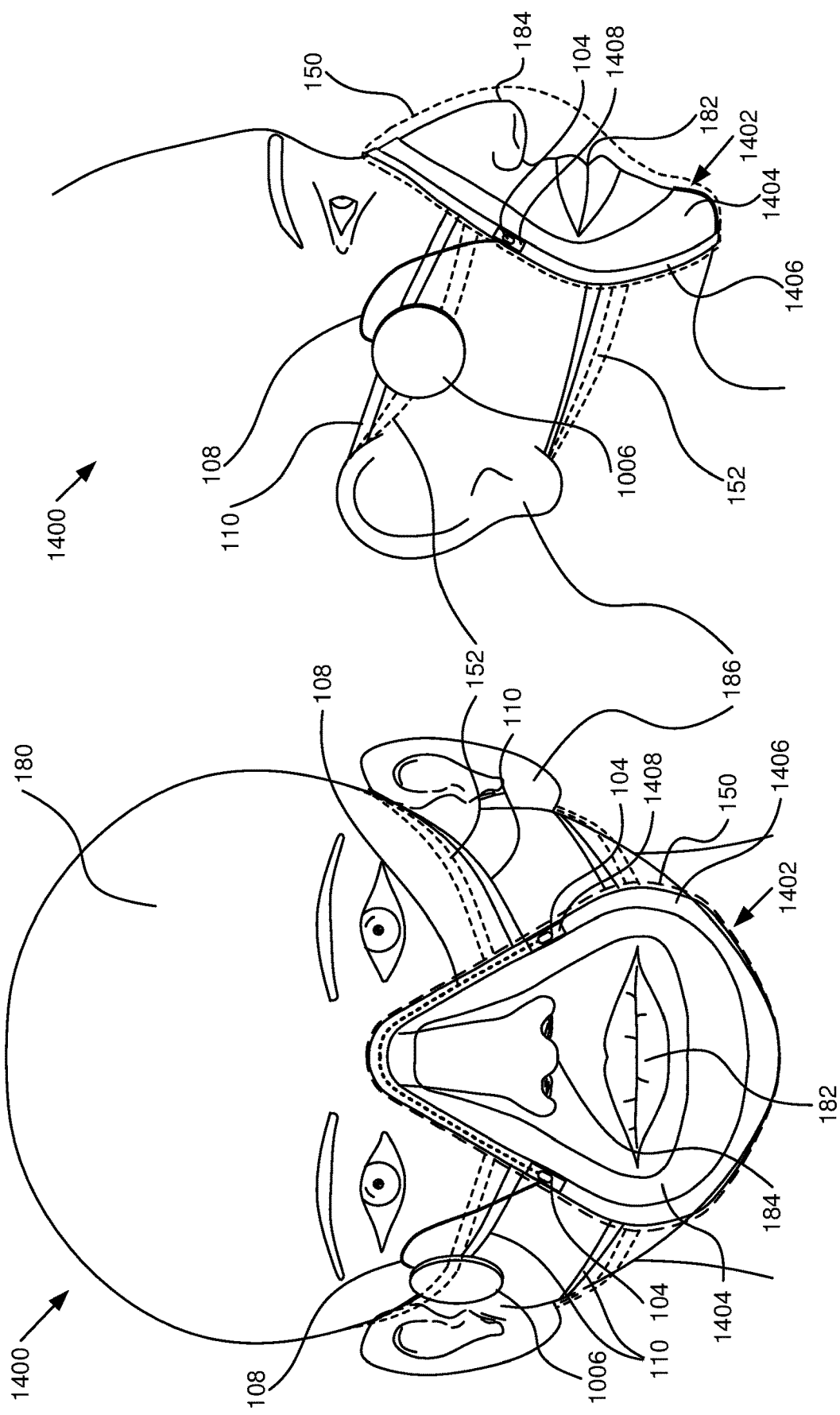
FIG. 14A is a front view illustrating an embodiment of an apparatus of a face covering that surrounds the mouth and nose of a user with two UV emitters.
FIG. 14B is a side view of the embodiment of FIG. 14A.

FIG. 14A is a front view illustrating an embodiment of an apparatus 1400 of a face covering 1402 that surrounds the mouth 182 and nose 184 of a user with two UV emitters 104 and FIG. 14B is a side view of the embodiment of FIG. 14A. The face covering 1402, in some embodiments, includes a contact portion 1404 that contacts the face of the user 180 and includes an extension section 1406 that extends away from the face of the user 180 at the outer edges of the contact portion 1404. In some embodiments, the extension section 1406 wraps back over the contact portion 1404 of the face covering 1402. For example, the face covering 1402 may be similar to a portion of a gas mask used for painting, for keeping dust from the face, etc. that includes a thin rubber portion in contact with the face and extends away from the portion that contacts the face toward an assembly with canaster filters. The contact portion 1404 and extension section 1406 could be shaped similarly but ends just past where the rubber extends away from the face of the user 180.

In one embodiment, the apparatus 1400 includes pads 1408 where the UV emitters 104 are attached to the pad and the pads 1408 are positioned between the contact portion 1404 and the UV emitters 104, for example to provide insulation from heat generated by the UV emitters 104. In another embodiment, the pads 1408 provide a means to secure the UV emitters 104 to the contact portion 1404 of the face covering 1402. In another embodiment, the pads 1408 provide a way to extend the UV emitters 104 out of a crease in the face covering 1402 formed by the contact portion 1404 and the extension section 1406 and the pads 1408 position the UV emitters 104 out away from the crease. The pads 1408, in various embodiments, may be neoprene, Lycra®, silicone rubber, Thermocline®, plastic, a heat sink 1316 or other material or a combination of materials. The pads 1408, in some embodiments, provide a stable and/or rigid platform for the UV emitters 104. The pads 1408 may also be compressible. One of skill in the art will recognize other materials suitable for the pads 1408 that provide a location for the UV emitters 104 to be mounted and are attachable to the material used for the face covering 1402.

In the depicted embodiment, straps 110 are connected to the face covering 1402 and a button cell battery case 1006 connected to the straps 110 and to the UV emitters 104 with a wire 108. In other embodiments, the apparatus 1400 includes more than one button cell battery cases 1006 and may include one or more other types of battery case(s) 106, 1206. In other embodiments, the apparatus 1400 includes a single UV emitter 104 and pad 1408.

In another embodiment, the extension section 1406 is replaced by a material different than the contact portion 1404. For example, the extension section 1406 may be stiffer than the contact portion 1404. For instance, the extension section 1408 may be made of neoprene, Lycra®, silicone rubber, Thermocline®, plastic or other material or a combination of materials. The extension section 1406, in some embodiments, is stiff enough to maintain its shape and/or to reduce stretching of the contact portion 1404 when the straps 110. In the embodiment, the pads 1408 may be eliminated and the UV emitters 104 may be attached directly to the extension section 1406. In other versions of the embodiment, the apparatus 1400 may include a heat sink 1316 under each UV emitter 104.

FIG. 15A is a front view illustrating an embodiment of another apparatus 1500 of a face covering 1502 that surrounds the mouth 182 and nose 184 of a user 180 with two UV emitters 104 and FIG. 15B is a side view of the embodiment of FIG. 15A. The apparatus 1500 is similar to the embodiments of the apparatus 1400 described above in relation to FIGS. 14A and 14B but do not have an extension section 1406 different from a contact portion 1404. The face covering 1502, in some embodiments, is all of one material, such as neoprene, Lycra®, silicone rubber, Thermocline®, plastic or other material. The face covering 1502 is in contact with the face of the user 180. In the depicted embodiment, pads 1508 are positioned between the face covering 1502 and the UV emitters 104. In other embodiments, the pads 1508 are not included. In other embodiments, the pads 1508 are replaced with heat sinks 1316. Straps 110 are connected to the face covering 1502 to hold the face covering 1502 to the face of the user 180. A button cell battery case 1006 is depicted and is connected to the straps 110 and to the UV emitters 104 with a wire 108. The button cell battery case 1006 may be replaced by other types of battery cases 106, 1206. In other embodiments, the apparatus 1500 includes more than one button cell battery cases 1006 or other types of battery cases 106, 1206. In other embodiments, the apparatus 1500 includes a single UV emitter 104 and/or pad 1508.

Figure 16C:
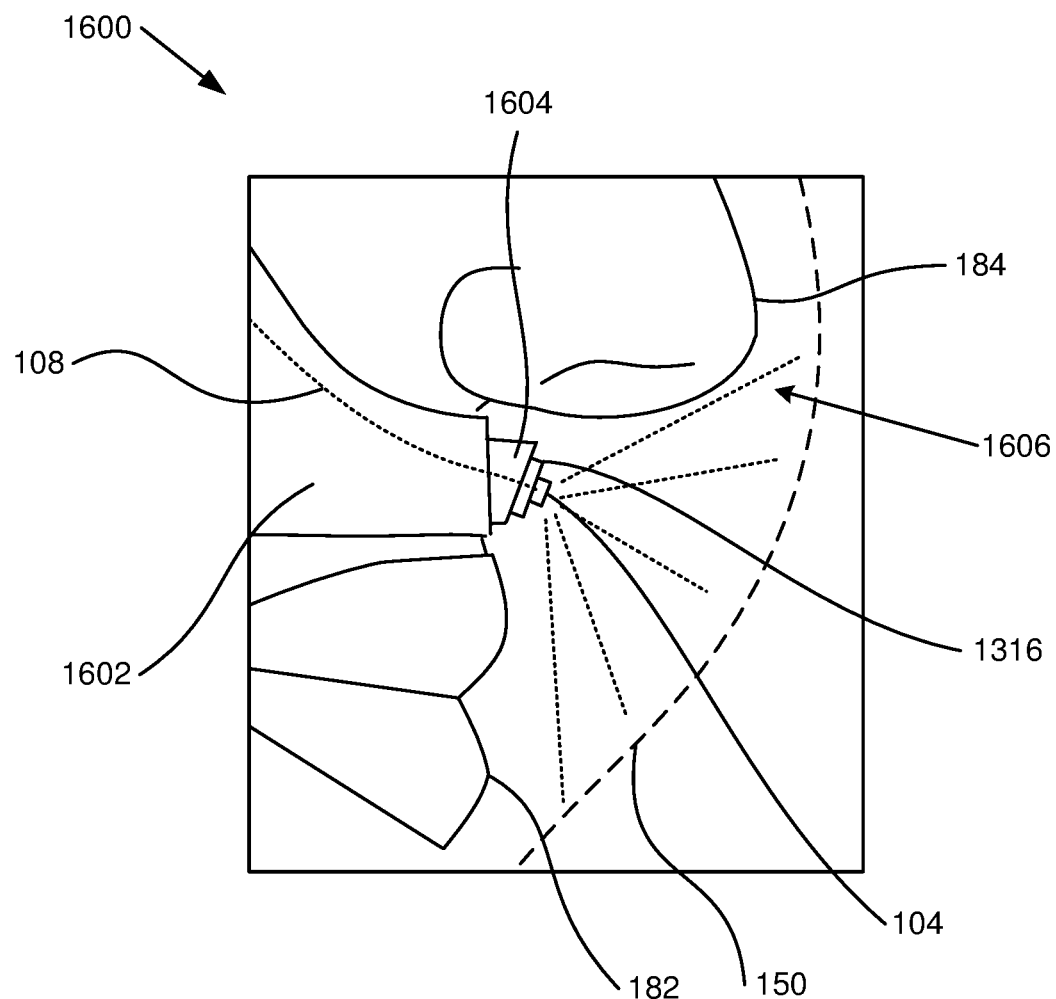
FIG. 16C is an enlarged view from FIG. 16B of the UV emitter and surroundings.

FIG. 16A is a front view illustrating an embodiment of another apparatus 1600 of a face covering 1602 that includes a single UV emitter 104 below the nose 184 of a user 180, FIG. 16B is a side view of the embodiment of FIG. 16A and FIG. 16C is an enlarged view from FIG. 16B of the UV emitter 104 and surroundings. In the embodiment, the apparatus 1600 includes a face covering 1602 shaped similarly to the face covering 1002 of FIGS. 10A and 10B, but the face covering 1602 has a single UV emitter 104 placed below the nose 184 of the user 180. To avoid UV light from the UV emitter 104 from shining directly on the nose 184, in some embodiments a block 1604 that is wedge-shaped is placed on the face covering 1602. In other embodiments, the block 1604 has a uniform thickness and is thick enough to position the UV emitter 104 to prevent UV light from the UV emitter 104 from shining directly on the nose 184 and/or mouth 182. In the embodiment depicted, a heat sink 1316 is between the block 1604 and the UV emitter 104.

The block 1604, when wedge-shaped, is shaped to change the angle of the UV emitter 104 to avoid UV light being directed at the nose 184 of the user 180, as depicted in FIGS. 16B and 16C. UV light is depicted as dashed lines 1606 and the UV emitter 104 emits UV light such that the UV light is angled as depicted in FIG. 13B. The block 1604 changes the UV light from the UV emitter 104 to avoid direct UV light on the nose 184 and mouth 182 of the user 180, as depicted in FIG. 16C. The block 1604, in various embodiments, is made of neoprene, plastic, rubber or any other material capable of connection to the face covering 1602 and holding the UV emitter 104 at a specific angle to the nose 184 and mouth 182 of the user 180. In some embodiments, the block 1604 is chosen for insulating properties to not conduct heat from the UV emitter 104 and heat sink 1316 being transferred to the face of the user 180. In other embodiments, the apparatus 1600 does not include the heat sink 1316 and the UV emitter 104 is mounted to the block 1604.

The apparatus 16 also includes a rigid strap holder 1608 positioned above or below the face covering 1602 where the straps 110 extend through the face covering 1602 to the rigid strap holder 1608. In some embodiments, the rigid strap holder 1608 includes holes and the strap 110 extends through the holes. In other embodiments, the straps 110 include clips, knots, etc. that are adjustable and provide a way to tighten or loosen the face covering 1602. The rigid strap holder 1608 may be made of plastic, cardboard, rubber, wood or other material that is more rigid than the face covering 1602. The rigid strap holder 1608 may be applied to other embodiments depicted herein.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An air sterilization apparatus comprising:
    a face covering shaped to fit under a facemask of a user and against skin of the face of the user, the face covering comprising a flexible material with an interior surface and an exterior surface, the face covering leaving nostrils and mouth of the user uncovered by the face covering such that when the face covering is in place with the interior surface against the face of the user, no portion of the face covering is over the nostrils and mouth of the user, wherein when the face covering is placed against the face of the user, the face covering conforms to the face of the user; and
    an ultraviolet ("UV") emitter mounted at a fixed angle on the exterior surface of the face covering, wherein the fixed angle of the UV emitter and a cutoff angle of UV light emitted from the UV emitter directs UV light from the UV emitter at a space immediately in front of the exposed mouth and nostrils of the user and away from exposed skin of the user, the UV light from the UV emitter comprising narrow-spectrum far ultraviolet ("UV-C") light, wherein the face covering is shaped so at least a portion of the face covering where the UV emitter is mounted on the exterior surface of the face covering comprises flexible material with the inside surface positioned against the face of the user and between the UV emitter and the face of the user.

2. The apparatus of claim 1, further comprising a battery case coupled to the UV emitter to power the UV emitter.

3. The apparatus of claim 2, wherein the battery case comprises a case shaped to hold button cell battery, a 9 volt battery and/or a 12 volt battery.

4. The apparatus of claim 1, further comprising a heat sink positioned between the UV emitter and the face covering.

5. The apparatus of claim 1, wherein the face covering covers an area of the face of the user under the facemask, the facemask shaped to cover the nose and mouth of the user.

6. The apparatus of claim 1, wherein the face covering has an opening that exposes nostrils of the user and/or an opening that exposes the mouth of the user, wherein UV light from the UV emitter is directed to avoid the nostrils and/or mouth of the user.

7. The apparatus of claim 1, wherein the face covering comprises a single UV emitter located below the nose and above the lips of the user, wherein the UV emitter is positioned and UV light from the UV emitter is angled so UV light from the UV emitter is in a direction to prevent UV light from the UV emitter from shining directly onto the nose and/or the mouth of the user.

8. The apparatus of claim 1, wherein material of the face covering has a nostril opening that exposes nostrils of the user and/or a mouth opening that exposes the mouth of the user, wherein the nostril and/or the mouth opening are covered with a mesh material and wherein the face covering covers a portion to a side of the mouth and nose of the user and is sized to prevent UV light from the UV emitter from shining directly on skin of the face of the user.

9. The apparatus of claim 1, wherein the UV emitter further emits light in a spectrum of light visible to humans.

10. The apparatus of claim 1, wherein the apparatus further comprises two or more UV emitters, each of the two or more UV emitters is positioned to emit light in a different portion of a volume between the face covering and the facemask.

11. The apparatus of claim 1, wherein the face covering further comprises straps attached to portions of the face covering on sides of the user's face, wherein the straps secure the face covering to the face of the user.

12. The apparatus of claim 11, wherein a battery case is secured to the straps.

13. The apparatus of claim 1, wherein the face covering comprises a material that shields the face of the user from UV light from the UV emitter.

14. The apparatus of claim 1, wherein the face covering covers a portion of the face of the user under the facemask and wherein one or more UV emitters are positioned on the face covering and aimed to avoid shining UV light directly on exposed skin of the face of the user.

15. An air sterilization apparatus comprising:
    a face covering shaped to fit under a separate facemask of a user and against skin of the face of the user, the face covering comprising a flexible material with an interior surface and an exterior surface, the face covering leaving nostrils and mouth of the user uncovered by the face covering such that when the face covering is in place with the interior surface against the face of the user, no portion of the face covering is over the nostrils and mouth of the user, wherein when the face covering is placed against the face of the user, the face covering conforms to the face of the user, wherein the face covering covers an area under the facemask;

one or more straps connected to portions of the face covering on sides of the user's face, the one or more straps configured to secure the face covering to the face of the user;

an ultraviolet ("UV") emitter mounted at a fixed angle on the exterior surface of the face covering, wherein the UV emitter is positioned between the face covering and the facemask, wherein the fixed angle of the UV emitter and a cutoff angle of UV light emitted from the UV emitter directs UV light from the UV emitter at a space immediately in front of the exposed mouth and nostrils of the user and away from exposed skin of the user, the UV light from the UV emitter comprising narrow-spectrum far ultraviolet ("UV-C") light, wherein the face covering is shaped so at least a portion of the face covering where the UV emitter is mounted on the exterior surface of the face covering comprises flexible material with the inside surface positioned against the face of the user and between the UV emitter and the face of the user; and a battery case electrically connected to the UV emitter to power the UV emitter, the battery case coupled to the one or more straps.

16. The apparatus of claim 15, wherein the UV emitter is a first UV emitter and further comprising a second UV emitter mounted to the exterior surface of the face covering, wherein the second UV emitter is electrically connected to the battery case or electrically connected to a second battery case, wherein the second battery case is coupled to the one or more straps.

17. An air sterilization apparatus comprising:

a face covering shaped to fit under a facemask of a user and against skin of the face of the user, comprising a flexible material with an interior surface and an exterior surface, the face covering leaving nostrils and mouth of the user uncovered by the face covering such that when the face covering is in place with the interior surface against the face of the user, no portion of the face covering is over the nostrils and mouth of the user, wherein when the face covering is placed against the face of the user, the face covering conforms to the face of the user;

one or more straps connected to portions of the face covering on sides of the user's face, the one or more straps configured to secure the face covering to the face of the user;

an ultraviolet ("UV") emitter mounted at a fixed angle on the exterior surface of the face covering, wherein the fixed angle of the UV emitter and a cutoff angle of UV light emitted from the UV emitter directs UV light from the UV emitter at a space immediately in front of the exposed mouth and nostrils of the user and away from exposed skin of the user, wherein the UV emitter emits narrow-spectrum far ultraviolet ("UV-C") light, wherein the face covering is shaped so at least a portion of the face covering where the UV emitter is mounted on the exterior surface of the face covering comprises flexible material with the inside surface positioned against the face of the user and between the UV emitter and the face of the user with no more than a thickness of the flexible face covering material between the UV emitter and the face of the user; and a battery case electrically connected to the UV emitter to power the UV emitter, the battery case coupled to the one or more straps on a side of the face of the user and outside the facemask, wherein the battery case comprises a case shaped to store a 9 volt battery, wherein the case comprises terminals to electrically connect the battery to wires connected to the UV emitter.

18. The apparatus of claim 1, wherein the face covering in an area where the UV emitter is mounted is made of a flexible material with no more than a thickness of the flexible face covering material between the UV emitter and the face of the user.

19. The apparatus of claim 1, wherein the face covering covers a portion of the face of the user where UV light from the UV emitter would directly shine on the face of the user without the portion of the face covering.

* * * * *